(12) United States Patent
Fowler et al.

(10) Patent No.: US 10,314,304 B2
(45) Date of Patent: *Jun. 11, 2019

(54) STABILIZED CHEMICAL COMPOSITION

(71) Applicant: Syngenta Participations AG, Basel (CH)

(72) Inventors: Jeffrey David Fowler, Greensboro, NC (US); Sejong Kim, Greensboro, NC (US)

(73) Assignee: Sygenta Participations AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/002,684

(22) Filed: Jun. 7, 2018

(65) Prior Publication Data

US 2018/0317477 A1 Nov. 8, 2018

Related U.S. Application Data

(62) Division of application No. 13/702,269, filed as application No. PCT/US2011/039384 on Jun. 7, 2011, now Pat. No. 10,004,226.

(60) Provisional application No. 61/486,581, filed on May 16, 2011, provisional application No. 61/352,246, filed on Jun. 7, 2010.

(51) Int. Cl.
*A01N 25/26* (2006.01)
*A01N 25/00* (2006.01)
*A01N 25/28* (2006.01)
*A01N 25/10* (2006.01)
*A01N 25/04* (2006.01)

(52) U.S. Cl.
CPC ............ *A01N 25/26* (2013.01); *A01N 25/04* (2013.01); *A01N 25/10* (2013.01); *A01N 25/28* (2013.01)

(58) Field of Classification Search
CPC ........ A01N 25/26; A01N 25/04; A01N 25/28; A01N 25/10
See application file for complete search history.

(56) References Cited

U.S. PATENT DOCUMENTS

| | | |
|---|---|---|
| 3,615,972 A | 10/1971 | Morehouse et al. |
| 4,016,110 A | 4/1977 | Cohrs et al. |
| 4,448,929 A | 5/1984 | Rodson et al. |
| 5,804,298 A | 9/1998 | Moy |
| 7,452,546 B2 | 11/2008 | Botts et al. |
| 2003/0198673 A1 | 10/2003 | Oshlack et al. |
| 2004/0082481 A1 | 4/2004 | Griffiths et al. |
| 2005/0288189 A1 | 12/2005 | Jacobson et al. |
| 2006/0193882 A1 | 8/2006 | Botts et al. |
| 2009/0181254 A1 | 7/2009 | White et al. |

FOREIGN PATENT DOCUMENTS

| | | |
|---|---|---|
| EP | 342685 A1 | 11/1989 |
| EP | 1922927 A1 | 5/2008 |
| GB | 2265594 A | 10/1993 |
| JP | 2007063181 A | 3/2007 |
| WO | 99/00013 A2 | 1/1999 |
| WO | 3016650 A1 | 2/2003 |
| WO | 2004054362 A1 | 7/2004 |
| WO | 2004092299 A1 | 10/2004 |
| WO | 2007033931 A1 | 3/2007 |
| WO | 2008/003049 A2 | 1/2008 |
| WO | 2008/030749 A2 | 3/2008 |
| WO | 2008032022 A2 | 3/2008 |
| WO | 2008071649 A2 | 6/2008 |
| WO | 2008089140 A1 | 7/2008 |
| WO | WO 2008/089140 * | 7/2008 |
| WO | 2008151781 A2 | 12/2008 |
| WO | 2009040359 A1 | 4/2009 |
| WO | 2009063257 A2 | 5/2009 |
| WO | 2009098232 A1 | 8/2009 |
| WO | 2010013250 A2 | 2/2010 |
| WO | 2011/137170 A1 | 11/2011 |

* cited by examiner

*Primary Examiner* — Johann R Richter
*Assistant Examiner* — Genevieve S Alley
(74) *Attorney, Agent, or Firm* — James Cueva

(57) ABSTRACT

Stabilized liquid agrochemical compositions are provided that comprise flowable, aqueous dispersion concentrates comprising a) a continuous aqueous liquid phase; b) at least one dispersed, solid phase comprising a dispersion of polymer particles having a mean particle size of at least one micron, wherein the outside surfaces of the particles comprise a colloidal solid material and wherein the particles have at least one agrochemically active ingredient distributed therein, optionally a non-porous particulate mineral that acts as a diffusion barrier to slow the release of the active ingredient, and optionally at least one non-cross-linkable mobile chemical such that the extraction of this chemical from the disperse phase renders it porous in a manner that allows the active ingredient to diffuse out. The colloidal solid is used to stabilize the polymerizable resin in an emulsion state during preparation. In one embodiment, the agrochemically active ingredient is a solid and is distributed within the dispersed solid phase or is a liquid and is distributed within the dispersed solid phase. The compositions of the invention can be used directly or with dilution to combat pests or as plant growth regulators.

18 Claims, No Drawings

STABILIZED CHEMICAL COMPOSITION

CROSS REFERENCE TO RELATED APPLICATIONS

This application is a divisional application of co-pending U.S. patent application Ser. No. 13/702,269 filed Dec. 5, 2012 which is a § 371 National Stage Entry of PCT/US11/39384 filed Jun. 7, 2011, which claims priority to U.S. Provisional Applications 61/486,581 filed May 16, 2011 and 61/352,246 filed Jun. 7, 2010.

BACKGROUND

The present invention relates to stabilized, liquid, chemical compositions, the preparation of such compositions and a method of using such compositions, for example, to combat pests or as plant growth regulators.

Agriculturally active ingredients (agrochemicals) are often provided in the form of concentrates suitable for dilution with water. Many forms of agricultural concentrates are known and these consist of the active ingredient and a carrier, which can include various components. Water-based concentrates are obtained by dissolving, emulsifying and/or suspending agriculturally active materials in water. Due to the relatively complex supply chain for crop protection agents, such concentrate formulations can be stored for long periods and may be subjected during storage and shipping to extreme temperature variations, high-shear and repetitive vibration patterns. Such supply chain conditions can increase the likelihood of formulation failure such as, for example, flocculation, thickening and sedimentation.

In some cases it may be desirable to combine different agrochemicals in a single formulation taking advantage of the additive properties of each separate agrochemical and optionally an adjuvant or combination of adjuvants that provide optimum biological performance. For example, transportation and storage costs can be minimized by using a formulation in which the concentration of the active agrochemical(s) is as high as is practicable and in which any desired adjuvants are "built-in" to the formulation as opposed to being separately tank-mixed. The higher the concentration of the active agrochemical(s) however, the greater is the probability that the stability of the formulation may be compromised, or that one or more components may phase separate. In addition formulation failure can be more challenging to avoid when multiple active ingredients are present because of physical or chemical incompatibilities between these chemicals such as, for example, when one active ingredient is an acid, a base, an oily liquid, a hydrophobic crystalline solid or a hydrophilic crystalline solid and the other active ingredient(s) has or have different properties.

It also may be desirable to improve the effectiveness of the agrochemicals by controlling the release rate of agrochemical into the application site from the formulation. In particular it may be desirable to combine agrochemicals in a single formulation and control their release rates independently, for instance in cases where the modes of action of the agrochemicals renders them antagonistic if both are delivered at the same rate.

In addition, spray tank mixes can contain a variety of chemicals and adjuvants that may interact and change the effectiveness of one or more of the agrochemicals included therein. Incompatibility, poor water quality and insufficient tank agitation can lead to reduced effectiveness of sprays, phytotoxicity and can affect equipment performance.

Pesticide-comprising aqueous polymer dispersions with a mean particle size of the dispersed particles of <1000 nm which are obtained from miniemulsion polymerization of ethylenically unsaturated monomers are known, for example, from US 2008/0171658. A limitation of polymer dispersions of this type is that the miniemulsions are stabilized by conventional surfactants and therefore have small particle size and high specific surface area, which can result in a rapid release of the agrochemical(s) contained therein.

Considering the variety of conditions and special situations under which agrochemical liquid concentrate formulation are stored, shipped and used around the world, there remains a need for aqueous polymer dispersions comprising agrochemicals, including water-soluble, water-dispersible or water-sensitive agrochemicals, having a mean particle size of the dispersed particles of >1000 nm and which provide additional stability benefits under at least some of those conditions and situations. There is a further need for such formulations having high loading that are stable when diluted with water under a wide range of field conditions. There is yet a further need for such formulations that have controlled release rates of agrochemicals into the application site from the formulation and that work in complex aqueous systems and under a variety of conditions.

Similar properties are required in formulations in non-agricultural fields, for instance for controlled delivery of pharmaceutically active ingredients, for controlled delivery of flavors from foods, for controlled delivery of dyes or pigments, for controlled release of fragrances from cosmetic or household products, or for controlled delivery of enzymes and detergents in cleaning products. In these industries and others there is a need for the ability to prepare stable formulations of components that can be released to the target site upon application.

SUMMARY OF THE INVENTION

Stabilized liquid agrochemical compositions are provided which comprise flowable, aqueous dispersion concentrates comprising: a) a continuous aqueous liquid phase; b) at least one dispersed solid phase comprising polymer particles having a mean particle size of at least one (1) micron, wherein the outside surfaces of the particles comprise a colloidal solid material and wherein the particles have at least one chemical agent distributed therein. The polymer particles are prepared from either a curable or polymerizable resin or a solidifiable thermoplastic polymer. In one embodiment, the colloidal solid material is present in the dispersed solid phase in an amount effective to stabilize the polymer resin in an emulsion state during the process which is used to prepare the dispersed phase. In another embodiment, surfactants are used in combination with the colloidal material in order to more flexibly control the size of the polymer particles. In another embodiment, the chemical agent is a solid and is distributed within the dispersed solid phase, or is a liquid and is distributed within the dispersed solid phase. In a further embodiment the continuous liquid phase is water or is a mixture of water and either a water-miscible liquid or a water-soluble solid. In another embodiment the polymer particles also contain a non-cross-linkable mobile chemical such that the extraction of this chemical from the dispersed solid phase renders it porous in a manner that allows the chemical agent to diffuse out from the dispersed phase. In another embodiment, the polymers forming the polymer particles contain hydrophilic groups that hydrate on exposure to water, thereby increasing the permeability of the polymer matrix and allowing the chemical agent to diffuse out from the dispersed phase. In another embodiment, the dispersed solid phase comprises polymer particles prepared by solidifying a thermoplastic polymeric resin, curing a thermoset resin or polymerizing a thermoplastic resin. When the at least one chemical agent is an agrochemically active ingredient, the compositions of the invention can be used directly or with dilution to combat pests or as plant growth regulators.

In accordance with one embodiment of the invention, it has been found that aqueous dispersion concentrates of agrochemically active ingredients in an aqueous liquid can be prepared by using polymerized, cured or solidified polymeric resin to entrap the agrochemically active ingredients in a polymer matrix when a colloidal solid is used to stabilize the polymer resin in an emulsion state during the curing reaction or solidification process. At least one agrochemically active ingredient can be distributed within the polymer matrix which is dispersed as particles within the continuous aqueous liquid phase. Other active ingredients may optionally be dispersed, dissolved, emulsified, microemulsified or suspended within the continuous phase.

The release rate of agrochemically active ingredients from the dispersed solid phase can be controlled by the optional incorporation within the dispersed phase of mobile non-cross-linkable molecules, where these molecules are chosen to be insoluble or partially soluble in the aqueous continuous phase, miscible or immiscible with the polymer resin that will form the particulate polymer matrix, soluble in water or some other medium to which the formulation will be exposed upon use, and of molecular dimensions such that the voids they create in the disperse phase upon extraction, allow the desired release of the agrochemically active ingredients. The mobile non-cross-linkable molecules may be present in the dispersed solid phase either as a molecular dispersion (if miscible with the polymer resin), or as discrete inclusions (if immiscible with the polymer resin).

The release rate of agrochemically active ingredients from the dispersed solid phase can be further controlled by the optional incorporation within the dispersed phase of non-porous particulate minerals as a diffusion barrier. For purposes of the present invention, non-porous means that the mineral lacks pores larger than individual molecules of the agrochemically active ingredients, such that the diffusion coefficient of the agrochemical through particles of the mineral is less than $10^{-15}$ m$^2$/s.

The aqueous dispersion concentrates of the invention have a usefully long period of protection for water-soluble, water-dispersible, water-sensitive and other agrochemicals such that the chemical and physical stability of the formulation is improved and which provides a practical utility in terms of storage, shipment and use. The dispersion concentrates of the invention also conveniently allow the combination of multiple active ingredients in a single formulation, irrespective of whether they are liquids or solids, by incorporating them separately or together in polymer matrix particles that are mutually physically compatible. The dispersion concentrates of the invention also provide the ability to control the release rate of the agrochemical into the target site from the concentrate or an end-use dilute formulation and to enhance biological performance against target pests.

The aqueous dispersion concentrates of the invention have utility also outside the agricultural field where there is need to prepare stable formulations and deliver chemical agents to a target site. For these purposes the agrochemicals may be replaced with other chemical agents as required. In the context of the present invention, chemical agents therefore include any catalyst, adjuvant, vaccine, genetic vector, drug, fragrance, flavor, enzyme, spore or other colony forming unit (CFU), detergent, dye, pigment, adhesive or other component where release of the chemical agent from the formulation is required. In addition the aqueous dispersion concentrates may be dried to prepare a powder or granular product as desired.

The polymerizable resins suitable for use in preparing the dispersed phase cured polymer matrix can be selected from monomers, oligomers or prepolymers which are polymerizable to either thermoset or thermoplastic polymer particles. In accordance with the invention, the disperse phase polymer matrix also can be formed by dissolving polymers in a volatile, water-immiscible solvent that also contains at least one agrochemical, stabilizing this solution in water as a Pickering emulsion using colloidal stabilizers, and then heating this emulsion to evaporate the volatile solvent and form a disperse solid phase of a thermoplastic polymer matrix. In addition, the disperse phase polymer matrix can be formed by dissolving or suspending at least one agrochemically active ingredient in a non-aqueous liquid mixture comprising a melt of at least one suitable thermoplastic polymer, emulsifying said dispersion concentrate into a heated aqueous liquid to a mean droplet size of 1-200 microns, which liquid also contains a colloidal solid as (Pickering) emulsion stabilizer; and cooling the emulsion to produce thermoplastic polymeric particles.

The present invention further relates to polymer particles comprising an entrapped agrochemical that is either homogeneously or non-homogeneously distributed within such particles or present in the form of domains within such particles and wherein the outside surface regions of the particles comprise a colloidal solid material.

The present invention also includes a method for combating or controlling pests or regulating the growth of plants at a locus such as soil or foliage which comprises treating said locus with a dispersion concentrate according to the invention or dispersing a concentrate according to the present invention in water or liquid fertilizer and treating said locus with the obtained diluted aqueous end-use formulation.

DETAILED DESCRIPTION OF THE INVENTION

Accordingly, in one embodiment, the aqueous liquid dispersion concentrate compositions of the present invention comprise:
a) a continuous, aqueous liquid phase, optionally comprising at least one chemical agent; and
b) at least one dispersed, solid phase comprising polymer particles having a mean particle size of at least one micron, wherein the outside surfaces of the particles comprise a colloidal solid material present in an amount effective to stabilize the polymer particles in an emulsion state during the process which is used to prepare the dispersed phase and wherein the polymer particles have at least one chemical agent distributed therein.

In one embodiment, the chemical agents are agrochemically active ingredients.

In one embodiment, the colloidal solid material is a Pickering colloid emulsion stabilizer.

In one embodiment, the polymer particles comprise an entrapped agrochemical that is either homogeneously on non-homogeneously distributed within such particles or present in the form of domains within such particles.

In the context of the present invention, mean particle or droplet size indicates the volume-weighted mean, commonly designated D(v,0.5).

In one embodiment, the agrochemically active ingredient is a solid and is distributed within the dispersed solid phase or is a liquid and is distributed within the dispersed solid phase.

In one embodiment, the agrochemically active ingredient (a.i.) in the dispersed phase is water-soluble, water-dispersible or water-sensitive.

In another embodiment, the dispersion concentrates for use in the liquid agrochemical compositions of the present invention are those that are formed using curing agents, monomers, oligomers, prepolymers or blends thereof that exhibit a slow curing or polymerization reaction when combined with the curing agents at ambient conditions. Particularly suitable are those curing agents, monomers, oligomers, prepolymers or blends thereof that exhibit no significant increase in viscosity under ambient conditions for a period of at least 15 minutes, more particularly 30 minutes, most particularly 1 hour, after mixing with the curing agent.

In accordance with one embodiment of the invention, polymerizable thermoset resins are understood to include all molecules that may be irreversibly polymerized or cured to form a polymeric matrix that does not melt or deform at elevated temperatures below the point of thermal decomposition. The polymerization reaction may be initiated thermally, by addition of chemical curing agents or by suitable irradiation to create radicals or ions such as by visible, UV, microwave or other electromagnetic irradiation, or electron beam irradiation. Examples include the phenolics, ureas, melamines, epoxies, polyesters, silicones, rubbers, polyisocyanates, polyamines and polyurethanes. In addition, bioplastic or biodegradable thermoset resins may be used including epoxy or polyester resins derived from natural materials such as vegetable oil, soy or wood and the like.

In accordance with another embodiment of the invention, polymerizable thermoplastic resins are understood to include all molecules that may be polymerized or cured to form a polymeric matrix that can melt or deform at elevated temperatures below the point of thermal decomposition. The polymerization reaction may be initiated thermally, by addition of chemical curing agents or by suitable irradiation to create radicals or ions such as by visible, UV or other electromagnetic irradiation, or electron beam irradiation. Examples of suitable ethylenically unsaturated monomers include styrene, vinyl acetate, a-methylstyrene, methyl methacrylate, those described in US 2008/0171658 and the like. Examples of thermoplastic polymers for polymer particles that can be prepared from in-situ mini-emulsion polymerization include polymethylmethacrylate, polystyrene, polystyrene-co-butadiene, polystyrene-co-acrylonitrile, polyacrylate, polyalkyl acrylate, polyalkyl acetate, polyacrylonitrile or their copolymers.

In accordance with yet another embodiment of the invention, solidifiable thermoplastic resins are understood to include all molecules that may be dissolved in a volatile solvent such that the solvent may be evaporated by heating to create a polymeric matrix that can melt or deform at elevated temperatures below the point of thermal decomposition. The volatile solvent is chosen to be immiscible with the continuous aqueous phase and sufficiently volatile that it can be conveniently removed from the composition by heating to a temperature below that where any significant decomposition occurs. Examples include polymers of the ethylenically unsaturated monomers described above, as well as polymers such as cellulose acetate, polyacrylates, polycaprolactone and polylactic acid. There may also be mentioned polymethylmethacrylate, polystyrene, polyethylvinyl acetate, cellulose acetate, polyacrylate, polyacrylonitrile, polyamide, polyalkyleneterephthalate, polycarbonate, polyester, polyphenylene oxide, polysulfone, polyimide, polyetherimide, polyurethane, polyvinylidene chloride, polyvinyl chloride, polypropylene and waxes, etc. In addition, bioplastic or biodegradable polymers such as thermoplastic starch, polylactic acid, polyhydroxy alkanoate, polycaprolactone, polyesteramide are also suitable for use in preparing polymer particles. Examples of volatile solvents include alkanes such as hexane and heptane, aromatic solvents such as benzene and toluene and halogenated solvents such as dicholoromethane and trichloromethane. Other examples of suitable polymers and solvents are described in WO2011/040956A1.

In accordance with the invention, the polymer particles of the dispersed phase have a mean particle size of from 1 to 200 microns, more particularly from 1 to 100 microns and most particularly, from 2 to 80 microns.

In one embodiment, suitable polymerizable resins and polymer solutions are those which are substantially immiscible with the aqueous liquid used in the continuous phase.

In the context of the present invention, a colloidal solid material is one whose properties of interest are determined by its surface interactions with other materials. Colloidal solids are therefore necessarily those with high specific surface area, typically above 10 $m^2/g$. For example, colloidal solids are able to stabilize emulsions of immiscible liquids, as described for instance in WO 2008/030749. When serving for this purpose, such colloidal solids may be called Pickering colloids, colloidal emulsion stabilizers, or other equivalent terms. Functional tests are known for whether a colloidal solid can stabilize an emulsion as used herein. One such test is described infra in paragraph 110 below. Not all colloidal solids are able to stabilize an emulsion of any given pair of immiscible liquids, and such a functional test may used by those skilled in the art to identify a suitable colloid.

As noted above, the release rate of agrochemically active ingredients from the dispersed solid phase can be further controlled by the optional incorporation within the dispersed phase of non-porous particulate minerals as a diffusion barrier. In some circumstances the same non-porous particulate mineral used as a diffusion barrier within the dispersed phase may also serve as the colloidal emulsion stabilizer. In this situation the particulate mineral may be added in two separate points within the preparation process as described below—firstly to the dispersed phase concentrate in order to become incorporated within the particles of the dispersed phase, and secondly to the aqueous continuous phase in order to stabilize the emulsion.

In another embodiment, the affinity of the aqueous liquids suitable for use in the continuous phase a) for the agrochemically active ingredient distributed in the dispersed solid phase b) is such that substantially all of the agrochemically active ingredient remains in the dispersed solid phase and substantially none migrates to the continuous phase. Those skilled in the art will readily be able to determine whether a particular aqueous liquid meets this criterion for a specific agrochemically active ingredient in question by following any standard test procedure for determining the partition coefficient of a compound (in this case, the agrochemically active ingredient of the dispersed phase) between the continuous phase and the dispersed solid phase. Accordingly, the dispersed solid phase b) is immiscible with the continuous phase a).

In a further embodiment, the aqueous liquids suitable for use in the continuous phase a) are solutions of water-soluble solutes in water.

Water-soluble solutes suitable for use in the continuous phase include salts such as halides, nitrates, sulfates, carbonates, phosphates, nitrites, sulfites, nitrides and sulfides of ammonium and of metals such as those of groups 1 to 12 of the periodic table. Other suitable solutes include sugars and osmolytes such as polysaccharides, proteins, betaines and amino acids.

In one embodiment, the aqueous liquids suitable for use in the continuous phase a) are mixtures of water and a substantially water-miscible non-aqueous liquid. In the context of the invention, the term "substantially water-miscible" means a non-aqueous liquid that forms a single phase when present in water at a concentration up to at least 50 wt %.

Substantially water-miscible non-aqueous liquids suitable for use in the continuous phase a) include, for example, propylene carbonate; a water-miscible glycol selected from ethylene glycol, diethylene glycol, triethylene glycol, propylene glycol, dipropylene glycol, tripropylene glycol, butylene glycol, hexylene glycol and polyethylene glycols having a molecular weight of up to about 800; an acetylated glycol such as di(propylene glycol) methyl ether acetate or propylene glycol diacetate; triethyl phosphate; ethyl lactate; gamma-butyrolactone; a water-miscible alcohol such as propanol or tetrahydrofurfuryl alcohol; N-methyl pyrrolidone; dimethyl lactamide; and mixtures thereof. In one embodiment, the non-aqueous, substantially water-miscible liquid used in the continuous phase a) is a solvent for at least one optional agrochemically active ingredient.

In another embodiment, the aqueous, substantially water-miscible liquid used in the continuous phase a) is fully miscible with water in all proportions. Alternatively, the aqueous, substantially water-miscible liquid used in the continuous phase a) is a waxy solid such as polyethylene glycol having a molecular weight above about 1000 and the mixture of this waxy solid with water is maintained in the liquid state by forming the composition at an elevated temperature.

Those skilled in the art will appreciate that the quantities of water and the nature and quantity of the non-aqueous, water-miscible liquid or water-soluble solute can be varied to provide mixed aqueous liquids suitable for use in the continuous phase a) and these quantities can be determined without undue experimentation. In one embodiment, the aqueous continuous phase comprises 5 to 95 wt %, more preferably 30 to 90 wt %, ethylene glycol with the balance being water. In another embodiment, the aqueous continuous phase comprises 5 to 95 wt %, more preferably 30 to 90 wt %, glycerol with the balance being water.

In one embodiment, when the concentrate is diluted in water, some of the agrochemical slowly diffuses out of the polymer matrix particles. The agrochemical release rate from the emulsified polymer particles in the spray tank can be adjusted, for example, by varying the size of the dispersed polymer particles in the concentrate, the concentration of active ingredient in the polymer, the pH of the spray tank dispersion, the optional inclusion of non-porous particulate minerals (as diffusion barriers) in the polymer matrix, and the amount and nature of the thermoplastic polymers or polymerizable resin including monomers, oligomers, prepolymers and/or hardeners used to form the polymer particles.

In this regard, the dispersed phase can also include one or more non-cross-linkable mobile chemicals such that the extraction of this chemical from the dispersed phase renders it porous in a manner that allows the chemical agent to diffuse out from the disperse phase. The mobile chemical may be chosen to diffuse out rapidly within the formulation concentrate, such that the polymer matrix is rendered so porous that the agrochemical is rapidly released upon dilution in water. Alternatively the mobile chemical may be chosen to be of limited solubility in the aqueous continuous phase, such that the mobile chemical diffuses out of the polymer matrix slowly after the formulation has been diluted in water or applied to its target location, so that the agrochemical is only substantially released at the target location. Examples include surfactants, solvents, oligomers, polymers, copolymers, acids, bases, natural or synthetic oils, natural or synthetic alcohols, substantially water-soluble compounds or substantially water-insoluble compounds. In a specific embodiment, the mobile chemical is selected such that it has limited solubility in a particular aqueous continuous phase, for instance an organic acid may be chosen that is substantially insoluble in an acidic aqueous continuous phase, yet upon dilution in water or application to the target site, the pH is higher than within the dispersion concentrate such that the organic acid (mobile chemical) is dissolved out of the polymer matrix rendering it porous and allowing the active ingredient to be released. In another specific embodiment the mobile chemical is selected such that it has limited solubility in aqueous environments but high solubility in waxy materials such as a plant cuticle, so that the mobile chemical is only substantially extracted from the matrix on contact with a plant leaf, and the active ingredient is then mainly released only on the leaf surface.

In another embodiment, a pH-sensitive release of the agrochemical active is achieved by creating a polymer matrix with excess amine groups. On dilution the amine groups hydrate, but the rate and extent of hydration increases at lower pH. The pH on dilution in the spray tank can be controlled by including within the dispersed phase base components, but after application the pH eventually becomes neutral and the release rate increases. Alternatively, a polymer matrix is created with excess acidic groups or other bases than amines. The nature of the pH sensitivity can be further adjusted by choosing acid or base groups of varying respective pKa or pKb values.

In another embodiment, the active ingredient release profile from the dispersed phase may be modified by incorporating cross-linkable monomers that contain hydrophilic groups such that on dilution into water the polymer matrix particles hydrate and expand so that the matrix becomes more permeable. In a particular embodiment, the cross-linkable monomers are glycerol diglycidyl ether epoxy resin. In another particular embodiment, the cross-linkable monomers are polypropyleneoxide diglycidyl ether epoxy resin.

The non-cross-linkable mobile chemical in the disperse phase may optionally be selected to also perform as a surfactant or dispersant within the liquid dispersion concentrate that is used to prepare the liquid agrochemical compositions of the present invention. If selected in this manner, the mobile chemical will adsorb to the surfaces of particles present in the dispersion concentrate and thereby stabilize the dispersion of those particles. This behaviour will be observable in at least one of the following ways: the particles will be distributed individually rather than as agglomerates within the dispersion concentrate when observed microscopically, the viscosity of the dispersion concentrate will be reduced when the mobile chemical is added, or the particles will have a greater tendency to remain within the disperse phase instead of being lost to the continuous phase when the liquid agrochemical compositions are prepared. Examples of suitable mobile chemicals useful for this purpose include copolymers of an α-olefin and an N-vinylpyrrolidone such as, for example, alkylated vinylpyrrolidone copolymers such as the Agrimers (e.g., Agrimer® AL-22, based on 1-ethenylhexadecyl-2-pyrrolidinone) (International Specialty Products (ISP) Corporation), or copolymers of an α-olefin and ethylene glycol such as, for example Atlox 4914 of Croda Corp, or organosilicon surfactants such as Silwet L-77 (Momentive Performance Chemicals).

In one embodiment, the aqueous liquid dispersion concentrate compositions of the present invention comprise a mixture of polymer particles each containing one or more than one chemical agents (such as an agrochemically active ingredient). Each one of the chemical agent(s) is contained within the same or different dispersed phase polymer particles, and each respective dispersed phase particle optionally includes a different mobile chemical and/or polymer matrix as described above, such that each chemical agent or agent mixture has a different release profile. Optionally each respective solid dispersed phase may have different particle sizes.

In one embodiment, the aqueous liquid dispersion concentrate compositions of the present invention comprise a solid phase in the form of finely divided, suspended polymer particles comprising a colloidal solid material at their outside surface and containing at least one agrochemically active ingredient, where the mean particle diameter of such polymer particles is generally below 200 microns, frequently below 100 microns, for example in the range from 1-200, particularly in the range from 1-100 and especially in the range from 2-80 microns.

The term "agrochemically active ingredient" refers to chemicals and biological compositions, such as those described herein, which are effective in killing, preventing, or controlling the growth of undesirable pests, such as, plants, insects, mice, microorganism, algae, fungi, bacteria, and the like (such as pesticidally active ingredients). The term may also apply to compounds that act as adjuvants to promote the uptake and delivery of other active compounds. The term may also apply to compounds that control the growth of plants in a desired fashion (e.g., plant growth regulators), to a compound which mimics the natural systemic activated resistance response found in plant species (e.g., plant activator) or to a compound that reduces the phytotoxic response to a herbicide (e.g., safener). If more than one is present, the agrochemically active ingredients are independently present in an amount that is biologically effective when the composition is diluted, if necessary, in a suitable volume of liquid carrier, e.g., water, and applied to the intended target, e.g., the foliage of a plant or locus thereof.

Examples of agrochemical active ingredients suitable for use within the continuous phase a) or disperse phase b) in accordance with the present invention include, but are not limited to: fungicides such as azoxystrobin, chlorothalonil, cyprodinil, difenoconazole, fludioxonil, mandipropamid, picoxystrobin, propiconazole, pyraclostrobin, tebuconazole, thiabendazole and trifloxystrobin; herbicides such as acetochlor, alachlor, ametryn, anilofos, atrazine, azafenidin, benfluralin, benfuresate, bensulide, benzfendizone, benzofenap, bicyclopyrone, bromobutide, bromofenoxim, bromoxynil, butachlor, butafenacil, butamifos, butralin, butylate, cafenstrole, carbetamide, chloridazon, chlorpropham, chlorthal-dimethyl, chlorthiamid, cinidon-ethyl, cinmethylin, clomazone, clomeprop, cloransulam-methyl, cyanazine, cycloate, desmedipham, desmetryn, dichlobenil, diflufenican, dimepiperate, dimethachlor, dimethametryn, dimethenamid, dimethenamid-P, dinitramine, dinoterb, diphenamid, dithiopyr, EPTC, esprocarb, ethalfluralin, ethofumesate, etobenzanid, fenoxaprop-ethyl, fenoxaprop-P-ethyl, fentrazamide, flamprop-methyl, flamprop-M-isopropyl, fluazolate, fluchloralin, flufenacet, flumiclorac-pentyl, flumioxazin, fluorochloridone, flupoxam, flurenol, fluridone, flurtamone, fluthiacet-methyl, indanofan, isoxaben, isoxaflutole, lenacil, linuron, mefenacet, mesotrione, metamitron, metazachlor, methabenzthiazuron, methyldymron, metobenzuron, metolachlor, metosulam, metoxuron, metribuzin, molinate, naproanilide, napropamide, neburon, norflurazon, orbencarb, oryzalin, oxadiargyl, oxadiazon, oxyfluorfen, pebulate, pendimethalin, pentanochlor, pethoxamid, pentoxazone, phenmedipham, pinoxaden, piperophos, pretilachlor, prodiamine, profluazol, prometon, prometryn, propachlor, propanil, propazine, propham, propisochlor, propyzamide, prosulfocarb, pyraflufen-ethyl, pyrazogyl, pyrazolynate, pyrazoxyfen, pyributicarb, pyridate, pyriminobac-methyl, quinclorac, siduron, simazine, simetryn, S-metolachlor, sulcotrione, sulfentrazone, tebutam, tebuthiuron, terbacil, terbumeton, terbuthylazine, terbutryn, thenylchlor, thiazopyr, thidiazimin, thiobencarb, tiocarbazil, triallate, trietazine, trifluralin, and vernolate; herbicide safeners such as benoxacor, dichlormid, fenchlorazole-ethyl, fenclorim, flurazole, fluxofenim, furilazole, isoxadifen-ethyl, mefenpyr; alkali metal, alkaline earth metal, sulfonium or ammonium cation of mefenpyr; mefenpyr-diethyl and oxabetrinil; insecticides such as abamectin, clothianidin, emamectin benzoate, gamma cyhalothrin, imidacloprid, cyhalothrin and its enantiomers such as lambda cyhalothrin, tefluthrin, permethrin, resmethrin and thiamethoxam; nematicides such as fosthiazate, fenamiphos and aldicarb.

Additionally, volatile agrochemically active ingredients such as those with a vapour pressure of at least 1 Pa at ambient temperature are also suitably entrapped in the dispersed phase b). Examples of such active ingredients include volatile nematicides such as methyl bromide, methyl iodide, chloropicrin and 1,3-dichloropropene.

In one embodiment, the active ingredients in the continuous phase may be in the state of a solution, an emulsion, a microemulsion, a microcapsule or a particle or fine particle. In the context of the present invention, a fine particle is one substantially smaller than the dimensions of the solid polymeric particles of the dispersed phase, such that a plurality (at least 10) of active ingredient particles are within each particle of the dispersed phase, whereas a non-fine particle is one only slightly smaller than the dimensions of the solid polymeric particles of the dispersed phase, such that each polymeric particle contains only a few active ingredient particles.

Further aspects of the invention include a method of preventing or combating infestation of plant species by pests, and regulating plant growth by diluting an amount of concentrate composition with a suitable liquid carrier, such as water or liquid fertilizer, and applying to the plant, tree, animal or locus as desired. The formulations of the present invention may also be combined in a continuous flow apparatus with water in spray application equipment, such that no holding tank is required for the diluted product.

The aqueous liquid dispersion concentrate compositions can be stored conveniently in a container from which they are poured, or pumped, or into which a liquid carrier is added prior to application.

The advantages of the aqueous liquid dispersion concentrate compositions of the present invention include: storage-stability for extended periods, for example 6 months or longer at room temperature; multiple agrochemicals of different physical states may be conveniently combined in dispersions of mutually compatible solid particles; the release profiles of agrochemicals may be flexibly and independently controlled; simple handling is made possible for users because dilution is made with water, or other liquid carrier, for preparation of application mixtures; reduced settling of the suspension during storage or on dilution; the compositions can easily be resuspended or redispersed with only a minor amount of agitation and are not susceptible to coalescence when dilution is made with fertilizer solutions for preparation of application mixtures.

The rate of application of the composition of the invention will depend on a number of factors including, for example, the active ingredients chosen for use, the identity of the pest to be controlled or the plants whose growth is to be inhibited and the formulations selected for use and whether the compound is to be applied to foliage, soil, for or root uptake or by chemigation. As a general guide, however, an application rate of from 1 to 2000 g active ingredient per hectare is suitable, in particular from 2 to 500 g active ingredient per hectare.

In one embodiment, suitable rates for the agrochemically active ingredients used in the inventive compositions are comparable to the existing rates given on the current product labels for products containing such actives. For example, Quadris® brand azoxystrobin can be applied at a rate of from 112 g to 224 g a.i./hectare and Quilt™ brand premix of azoxystrobin (75 g/L)/propiconazole(125 g/L) can be applied at a rate of from 0.75 -1.5 L/ha.

In one embodiment of the present invention, a further component may be present to control the pH of the water used to dilute the composition prior to use.

If a solid agrochemically active material is present, the solid active ingredient may be milled to the desired particle size prior to dispersion within the polymerizable resin (monomers, oligomers, and/or prepolymers, etc.) that will form the polymer matrix particles. The solid may be milled in a dry state using an air-mill or other suitable equipment as necessary, to achieve the desired particle size. The particle size may be a mean particle size of about 0.2 to about 20 microns, suitably about 0.2 to about 15 microns, more suitably about 0.2 to about 10 microns.

As used herein, the term "agrochemically effective amount" means the amount of an agrochemical active compound which adversely controls or modifies target pests or regulates the growth of plants (PGR). For example, in the case of herbicides, a "herbicidally effective amount" is that amount of herbicide sufficient for controlling or modifying plant growth. Controlling or modifying effects include all deviation from natural development, for example, killing, retardation, leaf burn, albinism, dwarfing and the like. The term plants refers to all physical parts of a plant, including seeds, seedlings, saplings, roots, tubers, stems, stalks, foliage and fruits. In the case of fungicides, the term "fungicide" shall mean a material that kills or materially inhibits the growth, proliferation, division, reproduction, or spread of fungi. As used herein, the term "fungicidally effective amount" or "amount effective to control or reduce fungi" in relation to the fungicidal compound is that amount that will kill or materially inhibit the growth, proliferation, division, reproduction, or spread of a significant number of fungi. As used herein, the terms "insecticide", "nematicide" or "acaricide" shall mean a material that kills or materially inhibits the growth, proliferation, reproduction, or spread of insects, nematodes or acarids, respectively. An "effective amount" of the insecticide, nematicide or acaricide is that amount that will kill or materially inhibit the growth, proliferation, reproduction or spread of a significant number of insects, nematodes or acarids.

In one aspect, as used herein, "regulating (plant) growth", "plant growth regulator", PGR, "regulating" or "regulation" includes the following plant responses; inhibition of cell elongation, for example reduction in stem height and internodal distance, strengthening of the stem wall, thus increasing the resistance to lodging; compact growth in ornamentals for the economic production of improved quality plants; promotion of better fruiting; increasing the number of ovaries with a view to stepping up yield; promotion of senescence of the formation of tissue enabling fruit to absciss; defoliation of nursery and ornamental bushes and trees for mail-order business in the fall; defoliation of trees to interrupt parasitic chains of infection; hastening of ripening, with a view to programming the harvest by reducing the harvest to one to two pickings and interrupting the food-chain for injurious insects.

In another aspect, "regulating (plant) growth", "plant growth regulator", "PGR", "regulating" or "regulation" also includes the use of a composition as defined according to the present invention for increasing the yield and/or improving the vigor of an agricultural plant. According to one embodiment of the present invention, the inventive compositions are used for improved tolerance against stress factors such as fungi, bacteria, viruses and/or insects and stress factors such as heat stress, nutrient stress, cold stress, drought stress, UV stress and/or salt stress of an agricultural plant.

The selection of application rates relative to providing a desired level of pesticidal activity for a composition of the invention is routine for one of ordinary skill in the art. Application rates will depend on factors such as level of pest pressure, plant conditions, weather and growing conditions as well as the activity of the agrochemically active ingredients and any applicable label rate restrictions.

The invention relates also to liquid agrochemical compositions comprising
  a) a continuous, aqueous liquid phase, optionally comprising at least one agrochemically active ingredient (for example, in the state selected from a solution or a dispersion such as emulsion, a microemulsion, and/or a suspension of microcapsules or fine particles); and
  b) at least one dispersed, solid phase comprising polymer particles prepared from either a curable or polymerizable resin or a solidafiable thermoplastic polymer, wherein the outside surfaces of the particles comprise a colloidal solid material and wherein the particles have at least one agrochemically active ingredient distributed therein.

A further aspect of the invention relates to a dilute aqueous spray composition for combating pests or regulating the growth of plants at a locus comprising
  a) a continuous aqueous phase comprising a suitable liquid carrier, such as water or a liquid fertilizer, in an amount sufficient to obtain the desired final concentration of each of the active ingredients in the spray composition;
  b) at least one dispersed, solid phase comprising polymer particles prepared from either a cureable or a polymerizable resin or a solidifiable thermoplastic polymer, wherein the outside surfaces of the particles comprise a colloidal solid material and wherein the particles have at least one agrochemically active ingredient distributed therein; and c) optionally, at least one agrochemically active ingredient dispersed, dissolved, suspended, microemulsified and/or emulsified in the liquid carrier.

In another embodiment, the invention relates to a dilute pesticidal and/or PGR composition for ultra low volume (ULV) application comprising:
  a) a continuous phase comprising a carrier solvent having a flash point above 55° C. in an amount sufficient to obtain the desired final concentration of each of the active ingredients in the ULV composition;
  b) at least one dispersed, solid phase comprising polymer particles prepared from either a cureable or a polymerizable resin or a solidifiable thermoplastic, wherein the outside surfaces of the particles comprise a colloidal solid material and wherein the particles have at least one agrochemically active ingredient distributed therein.

The invention relates also to a method for combating or preventing pests in crops of useful plants or regulating the growth of such crops, said method comprising:
  1) treating the desired area, such as plants, the plant parts or the locus thereof with a concentrate composition comprising:
    a) a continuous aqueous liquid phase, optionally comprising at least one agrochemically active ingredient, and also optionally comprising at least one acidic or basic component;
    b) at least one dispersed, solid phase comprising polymer particles prepared from either a cureable or a polymerizable resin or a solidifiable thermoplastic, wherein the outside surfaces of the particles comprise a colloidal solid material and wherein the particles have at least one agrochemically active ingredient distributed therein; or
  2) diluting the concentrate composition, if necessary, in a suitable carrier, such as water, liquid fertilizer or a carrier solvent having a flash point above 55° C., in an amount sufficient to obtain the desired final concentration of each of the agrochemically active ingredients; and then treating the desired area, such as plants, the plant parts or the locus thereof with the dilute spray or ULV composition.

The term plants refers to all physical parts of a plant, including seeds, seedlings, saplings, roots, tubers, stems, flowers, stalks, foliage and fruits. The term locus refers to where the plant is growing or is expected to grow.

The composition according to the invention is suitable for all methods of application conventionally used in agriculture, e.g. pre-emergence application, post-emergence application, post-harvest and seed dressing. The compositions according to the invention are suitable for pre- or post-emergence applications to crop areas.

The compositions according to the invention are suitable especially for combating and/or preventing pests in crops of useful plants or for regulating the growth of such plants. Preferred crops of useful plants include canola, cereals such as barley, oats, rye and wheat, cotton, maize, soya, sugar beets, fruits, berries, nuts, vegetables, flowers, trees, shrubs and turf. The components used in the composition of the invention can be applied in a variety of ways known to those skilled in the art, at various concentrations. The rate at which the compositions are applied will depend upon the particular type of pests to be controlled, the degree of control required, and the timing and method of application.

Crops are to be understood as also including those crops which have been rendered tolerant to herbicides or classes of herbicides (e.g. ALS-, GS-, EPSPS-, PPO-, ACCase and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Crop areas are areas of land on which the cultivated plants are already growing or in which the seeds of those cultivated plants have been sown, and also areas of land on which it is intended to grow those cultivated plants.

Other active ingredients such as herbicide, plant growth regulator, algaecide, fungicide, bactericide, viricide, insecticide, acaricide, nematicide or molluscicide may be present in the formulations of the present invention or may be added as a tank-mix partner with the formulations.

The compositions of the invention may further comprise other inert additives. Such additives include thickeners, flow enhancers, dispersants, emulsifiers, wetting agents, anti-foaming agents, biocides, lubricants, fillers, drift control agents, deposition enhancers, adjuvants, evaporation retardants, freeze protecting agents, insect attracting odor agents, UV protecting agents, fragrances, and the like. The thickener may be a compound that is soluble or able to swell in water, such as, for example, polysaccharides of xanthans (e.g., anionic heteropolysaccharides such as RHODOPOL® 23 (Xanthan Gum)(Rhodia, Cranbury, N.J.)), alginates, guars or celluloses; synthetic macromolecules, such as modified cellulose-based polymers, polycarboxylates, bentonites, montmorillonites, hectonites, or attapulgites. The freeze protecting agent may be, for example, ethylene glycol, propylene glycol, glycerol, diethylene glycol, saccharose, water-soluble salts such as sodium chloride, sorbitol, triethylene glycol, tetraethylene glycol, urea, or mixtures thereof. Representative anti-foam agents are silicone oils, polydialkylsiloxanes, in particular polydimethylsiloxanes, fluoroaliphatic esters or perfluoroalkylphosphonic/perfluoroalkylphosphonic acids or the salts thereof and mixtures thereof. Suitable antifoams are polydimethylsiloxanes, such as Dow Corning® Antifoam A, Antifoam B or Antifoam MSA. Representative biocides include 1,2-benzisothiazolin-3-one, available as PROXEL® GXL (Arch Chemicals).

The compositions of the invention may be mixed with fertilizers and still maintain their stability.

The compositions of the invention may be used in conventional agricultural methods. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

Within the scope of the present invention are four different methods of producing dispersed phase polymeric particles containing chemical agents, which are described in a manner wherein the chemical agents are agriculturally active ingredients. Each method results in a dispersed phase that comprises a solid polymer matrix with at least one agriculturally active ingredient distributed therein, a colloidal solid material at the surface, optionally a non-cross-linkable mobile chemical such that the extraction of this chemical from the dispersed phase renders it porous in a manner that allows the agrochemically active ingredient(s) to diffuse out from the dispersed phase, optionally a polymer matrix with hydrophilic groups that hydrate on exposure to water and render the matrix permeable in a manner that allows the agrochemically active ingredient(s) to diffuse out from the dispersed phase, and optionally a non-porous mineral that renders the dispersed phase more impermeable to the agrochemically active ingredient(s).

The first method comprises the following steps:
1. preparing a dispersion concentrate by dissolving or suspending at least one agrochemically active ingredient in a non-aqueous curable liquid mixture comprising at least one suitable cross-linkable resin (comprising monomers, oligomers, prepolymers or blends thereof), optionally where the resin contains hydrophilic groups, optionally a suitable hardener, catalyst or initiator, and one or more optional components selected from non-porous particulate minerals as diffusion barrier and/or non-crosslinkable mobile chemicals,
2. emulsifying said dispersion concentrate in to an aqueous liquid to a mean droplet size of 1-200 microns, which liquid also contains a colloidal solid as (Pickering) emulsion stabilizer, and, optionally, certain suitable hardener, catalyst or initiator capable of diffusing into the dispersed uncured resin droplets; and
3. effecting crosslinking or cure of the cross-linkable resin mixture to produce cured thermoset polymeric particles.

The second method is substantially identical to the first, except that the dispersion concentrate comprises as non-aqueous liquid a polymerizable resin instead of a cross-linkable resin. Instead of a curing reaction in step 3, the dispersed phase particles are formed by a polymerization reaction, so that the resulting dispersed phase comprises thermoplastic polymeric particles rather than thermoset polymeric particles.

The third method comprises the following steps:
1. dissolving or suspending at least one agrochemically active ingredient in a non-aqueous liquid mixture comprising at least one suitable solidifiable polymer dissolved in a volatile solvent, and one or more optional components selected from non-porous particulate minerals as diffusion barrier and/or non-crosslinkable mobile chemicals;
2. emulsifying said solution in to an aqueous liquid to a mean droplet size of 1-200 microns, which liquid also contains a colloidal solid as (Pickering) emulsion stabilizer; and
3. effecting evaporation of the volatile solvent by heating the emulsion to a temperature of about 30-120° C. for about 0.1-10 hr to produce solid thermoplastic polymer particles.

The fourth method of preparation comprises the following steps:
1. preparing a dispersion concentrate by dissolving or suspending at least one agrochemically active ingredient in a non-aqueous curable liquid mixture comprising a melt of at least one suitable solidifiable thermoplastic polymer, and one or more optional components selected from non-porous particulate minerals as diffusion barrier and/or non-crosslinkable mobile chemicals,
2. emulsifying said dispersion concentrate in to a heated aqueous liquid to a mean droplet size of 1-200 microns, which liquid also contains a colloidal solid as (Pickering) emulsion stabilizer; and
3. cooling the emulsion to produce thermoplastic polymeric particles.

In one embodiment, the dispersion concentrate is prepared by:
a. dissolving or suspending at least one agrochemically active ingredient in a non-aqueous liquid mixture (premix) comprising at least one suitable curable or polymerizable resin (comprising monomers, oligomers, prepolymers or blends thereof), optionally a suitable hardener, catalyst or initiator, and one or more optional components selected from non-porous particulate minerals (as diffusion barrier) and/or non-crosslinkable mobile chemicals;
b. emulsifying said solution or suspension in to an aqueous liquid to a mean droplet size of 1-200 microns, which liquid also contains a colloidal solid as (Pickering) emulsion stabilizer, and, optionally, certain suitable hardener, catalyst or initiators capable of diffusing into the dispersed uncured or unpolymerized resin droplets; and
c. effecting cros slinking, cure or polymerization of the resin mixture to produce cured thermoset or polymerized thermoplastic resin polymer particles having at least one agriculturally active ingredient distributed therein and at least one colloidal solid material at their surfaces and that after curing are dispersed in the aqueous liquid.

In one embodiment, the dispersion concentrate is prepared by adding the hardener through the continuous phase, after the Pickering emulsion is formed, so that the dispersed phase premix is incapable of curing. Alternatively a first very slow-reacting hardener can be used in the dispersion concentrate, and then a second fast-curing hardener, an accelerator or catalyst can be added through the continuous phase. These second agents are added to the continuous phase after the dispersed phase is emulsified, so they must be chosen to be miscible in the continuous phase. Suitable fast cure water-miscible hardeners include diethylene triamine, triethylene tetramine, xylene diamine, polyethylene glycol diamine, and polyoxypropylene diamine. Mixtures of hardeners may also be employed for extra flexibility.

In one embodiment, the dispersion concentrate is prepared by adding a premix of the dispersed phase to a premix of the continuous phase, wherein:
1) the premix of the dispersed phase is prepared by blending with a high shear mixer: at least one agriculturally active ingredient, at least one suitable curable or polymerizable resin monomer, oligomer, prepolymer or blend thereof, a suitable hardener, catalyst or initiator, an optional non-crosslinkable mobile chemical, and an optional particulate non-porous mineral as diffusion barrier;
2) the premix of the continuous phase is prepared by blending with low shear mixer: an aqueous liquid with a colloidal solid as an emulsion stabilizer.

The resulting mixtures of the dispersed phase premix and the continuous phase premix are stirred under high shear conditions for a suitable time to form a Pickering emulsion and then heated or exposed to light or other electromagnetic radiation conditions (UV, microwave), as needed, in order to polymerize the dispersed phase. The shear rate and duration of the emulsification may be readily determined by one skilled in the art, guided by the following observations: if the shear rate is too low, the emulsion and resulting polymer matrix particles are relatively coarse and may be larger than desired; if the shear rate is instead too high or of too long a duration, the emulsion stabilizing colloid eventually becomes so depleted from the continuous phase that any new interfacial surface between the dispersed and continuous phases is effectively unprotected, at which point rapid coalescence or heteroflocculation of the dispersed phase occurs and the Pickering emulsion is effectively lost.

In one embodiment, the mixture of the dispersed phase premix and the continuous phase premix is stirred under high shear conditions for 5-10 min and heated to a temperature of about 30-120° C. for about 0.1-10 hr in order to effect the curing reaction.

In one embodiment, the dispersion concentrate is prepared by:
a. dissolving or suspending at least one agrochemically active ingredient in a non-aqueous liquid mixture comprising at least one suitable polymer dissolved in a volatile solvent, and one or more optional components selected from non-porous particulate minerals (as diffusion barrier) and/or non-crosslinkable mobile chemicals;
b. emulsifying said solution in to an aqueous liquid to a mean droplet size of 1-200 microns, which liquid also contains a colloidal solid as (Pickering) emulsion stabilizer; and
c. effecting evaporation of the volatile solvent by heating the emulsion to a temperature of about 30-120° C. for about 0.1-10 hr to produce solid thermoplastic polymer particles having at least one agriculturally active ingredient distributed therein and colloidal solids at their surfaces and that are dispersed in the aqueous liquid. If necessary more liquid may be added to the continuous phase to replace any liquid lost during the evaporation process.

Suitable polymerizable resins for use in preparing the solid polymer particles of the dispersed solid phase include thermosets such as epoxy resins, phenolic resins, aminoplast resins and polyester resins.

Other suitable polymerizable resins for use in preparing the solid polymer particles of the dispersed solid phase include thermoplastics resins such as styrenes, methyl methacrylates, and acrylics.

Suitable thermoplastic polymers include polymers of the thermoplastic resins described above, as well as polymers such as cellulose acetate, polyacrylates, polycaprolactone and polylactic acid.

With respect to the epoxies, all customary di-and polyepoxide monomers, prepolymers or blends thereof are suitable epoxy resins for the practice of this invention. In one embodiment, suitable epoxy resins are those that are liquid at ambient temperature. The di- and polyepoxides may be aliphatic, cycloaliphatic or aromatic compounds. Typical examples of such compounds are the diglycidyl ethers of bisphenol A glycerol or resorcinol, the glycidyl ethers and β-methylglycidyl ethers of aliphatic or cycloaliphatic diols or polyols, including those of hydrogenated bisphenol A, ethylene glycol, 1,2-propanediol, 1,3-propanediol, 1,4-butanediol, diethylene glycol, polyethylene glycol, polypropylene glycol, glycerol, trimethylolpropane or 1,4-dimethylolcyclohexane or of 2,2-bis(4-hydroxycyclohexyl) propane, the glycidyl ethers of di- and polyphenols, typically resorcinol, 4,4'-dihydroxydiphenylmethane, 4,4'-dihydroxydiphenyl-2,2-propane, novolaks and 1,1,2,2-tetrakis(4-hydroxyphenyl)ethane, Further examples are N-glycidyl compounds, including diglycidyl compounds of ethylene urea, 1,3-propylene urea or 5-dimethylhydantoin or of 4,4'-methylene-5,5'-tetramethyldihydantoin, or those such as triglycidyl isocyanurate, or biodegradable/bio-derived epoxies (vegetable oil-based).

Further glycidyl compounds of technical importance are the glycidyl esters of carboxylic acids, especially di-and polycarboxylic acids. Typical examples are the glycidyl esters of succinic acid, adipic acid, azelaic acid, sebacic acid, phthalic acid, terephthalic acid, tetraand hexahydrophthalic acid, isophthalic acid or trimellitic acid or of partially polymerized, e.g. dimerised, fatty acids.

Exemplary of polyepoxides that differ from glycidyl compounds are the diepoxides of vinylcyclohexene and dicyclopentadiene, 3-(3',4'-epoxycyclohexyl)-8,9-epoxy-2,4-dioxaspiro[5.5]undecane, the 3',4'-epoxycyclohexylmethyl ester of 3,4-epoxycyclohexanecarboxylic acid, butadiene diepoxide or isoprene diepoxide, epoxidized linoleic derivatives or epoxidized polybutadiene.

Other suitable epoxy resins are diglycidyl ethers or advanced diglycidyl ethers of dihydric phenols or dihydric aliphatic alcohols of 2 to 4 carbon atoms, preferably the diglycidyl ethers or advanced diglycidyl ethers of 2,2-bis (4-hydroxyphenyl)propane and bis(4-hydroxyphenyl)methane or a mixture of these epoxy resins.

Suitable epoxy resin hardeners for the practice of this invention may be any suitable epoxy resin hardener, typically selected from primary and secondary amines and their adducts, cyanamide, dicyandiamide, polycarboxylic acids, anhydrides of polycarboxylic acids, polyamines, polyaminoamides, polyadducts of amines and polyepoxides and polyols.

A variety of amine compounds (mono, di or polyamines) can be used as a hardener such as aliphatic amines (diethylene triamine, polyoxypropylene triamine etc), cycloaliphatic amines (isophorone diamine, aminoethyl piperazine or diaminocyclohexane etc), or aromatic amines (diamino diphenyl methane, xylene diamine, phenylene diamine etc). Primary and secondary amines broadly can serve as hardening agents while tertiary amines generally act as catalysts.

Although epoxy hardeners are typically amines, other options exist and these will give extra flexibility to accommodate chemical agents that might be unstable or soluble in the presence of amine, or allow a broader range of cure rates to be achieved.

For example, other suitable hardeners are anhydrides of polycarboxylic acids, typically phthalic anhydride, nadic anhydride, methylnadic anhydride, methyltetrahydrophthalic anhydride, methylhexahydrophthalic anhydride and, in addition, tetrahydrophthalic anhydride and hexahydrophthalic anhydride.

In accordance with the invention, Pickering colloidal emulsion stabilizers of any type may be used to stabilize emulsions prior to the step of solidifying the dispersed phase into a solid polymer matrix, regardless of polymer matrix type, where the dispersed phase contains a chemical agent such as an agrochemical active ingredient, and optionally where the dispersed phase contains a means to control the matrix permeability and thereby the agrochemical active ingredient release rate upon application.

More specifically, solids, such as silicas and clays, have been taught in the literature for use as viscosity modifiers in agrochemical formulations to inhibit gravity-driven sedimentation or cream separation by forming a network or gel throughout the continuous phase, thereby increasing the low-shear viscosity, and slowing the movement of small particles, surfactant micelles or emulsion droplets. The colloidal solids of the present invention instead serve as a processing aid to stabilize the droplets containing the resin monomers during cure by adsorbing to the transient liquid-liquid interface, thereby forming a barrier around the curing droplets so that contacting or neighbouring curing droplets are not able to coalesce, irrespective of whether or not the curing droplets have collected in a sediment or a cream layer. It is possible to distinguish the two different functions—rheological modification or emulsion stabilization, by a functional test such as described below. The effectiveness of the colloidal solid in stabilizing the emulsions of curing polymer droplets depends on particle size, particle shape, particle concentration, particle wettability and the interactions between particles. The colloidal solids must be small enough so that they can coat the surfaces of the dispersed curing liquid polymer droplets, and the curing liquid droplets must be sufficiently small for acceptable dispersion stability against sedimentation of the resulting solid polymer particles if the dispersion concentrate containing such particles is diluted for use. The final polymer particles (and hence, the colloidal solids) will also need to be small enough to provide an acceptably even product distribution at the target site. The colloidal solid also must have sufficient affinity for both the liquids forming the dispersed and continuous phases so that they are able to adsorb to the transient liquid-liquid interface and thereby stabilize the emulsion during cure. This wetting characteristic, particle shape and suitability for Pickering-type emulsion stabilization may be readily assessed by preparing a control formulation lacking the colloidal solid as emulsion stabilizer. In such a case the curing liquid polymer droplets coalesce and form a consolidated mass instead of a dispersion of fine solid polymer particles.

In one embodiment, the colloidal solids have a number-weighted median particle size diameter as measured by scanning electron microscopy of 0.01-2.0 microns, particularly 0.5 microns or less, more particularly 0.1 microns or less.

A wide variety of solid materials may be used as colloidal stabilizers for preparing the dispersions of the present invention including carbon black, metal oxides, metal hydroxides, metal carbonates, metal sulfates, polymers, silica and clays. Suitable colloidal stabilizers are insoluble in any of the liquid phases present in preparation of the concentrate formulation. If an agrochemical active ingredient has suitably low solubility in any liquid used to dilute the final composition, and in both the continuous and (transient) dispersed liquid phases, that is below about 100 ppm at room temperature, and can be prepared at a suitable particle size, and has suitable wetting properties for the transient liquid-liquid interface as described above, then it is also possible that this active ingredient can serve as the colloidal stabilizer. Examples of particulate inorganic materials are oxy compounds of at least one of calcium, magnesium, aluminium and silicon (or derivatives of such materials), such as silica, silicate, marble, clays and talc. Particulate inorganic materials may be either naturally occurring or synthesized in reactors. The particulate inorganic material may be a mineral chosen from, but not limited to, kaolin, bentonite, alumina, limestone, bauxite, gypsum, magnesium carbonate, calcium carbonate (either ground or precipitated), perlite, dolomite, diatomite, huntite, magnesite, boehmite, sepiolite, palygorskite, mica, vermiculite, illite, hydrotalcite, hectorite, halloysite and gibbsite. Further suitable clays (for example aluminosilicates) include those comprising the kaolinite, montmorillonite or illite groups of clay mineral. Other specific examples are attapulgite, laponite and sepiolite. Polymers that flocculate the colloids (such as xanthan in the case of colloidal kaolin) can also improve the stability of Pickering emulsions.

In one embodiment, non-porous particulate inorganic materials are distributed within the polymer particles along with the agrochemically active ingredient to serve as an optional diffusion barrier. The diffusion barrier is prepared by dissolving or suspending such materials along with the (e.g., water-sensitive) agriculturally active ingredient in the non-aqueous curable liquid mixture that is used to prepare the thermoset or thermoplastic resin polymer particles which serve as dispersed phase b). Suitable non-porous particulate diffusion barrier materials include carbon black, metal oxides, metal hydroxides, metal carbonates, metal sulfates, polymers, silica, mica and clays.

In one aspect of the invention, the particulate inorganic material is kaolin clay. Kaolin clay is also referred to as china clay or hydrous kaolin, and contains predominantly mineral kaolinite ($Al_2Si_2O_5(OH)_4$), a hydrous aluminium silicate (or aluminosilicate).

In one aspect of the invention, the particulate inorganic material may be surface modified. Surface-modified means that the inorganic particle surface has been modified so as to have reactive groups. The surface of the particles may be modified using a wide variety of chemicals, with the general structure X—Y—Z, in which X is a chemical moiety with a high affinity for the particle surface; Z is a (reactive) chemical moiety with a desired functionality; and Y is a chemical moiety that links X and Z together.

X may be, for example, an alkoxy-silane group such as tri-ethoxysilane or tri-methoxysilane or trichlorosilane, which is particularly useful when the particles have silanol (SiOH) groups on their surface. X may also be, for example, an acid group (such as a carboxylic or an acrylic acid group) which is particularly useful when the particles have basic groups on their surface. X may also be, for example, a basic group (such as an amine group), an epoxy group, or an unsaturated group (such as an acrylic or vinyl group).

Y can be any chemical group that links X and Z together, for example a polyamide, a polyisocyanate, a polyester or an alkylene chain; more suitably it is an alkylene chain; and even more suitably it is a $C_{2-6}$ alkylene chain, such as ethylene or propylene.

Reactive groups Z can be selected from any groups, and may be different from Y, which can be used to react with a cross-linker.

The type and amount of colloidal solid is selected so as to provide acceptable physical stability of the composition during cure, polymerization, solvent evaporation or other polymer solidification processes. This can readily be determined by one of skill in the art by routine evaluation of a range of compositions having different amounts of this component. For example, the ability of the colloidal solids to stabilize the composition can be verified by preparing a test sample with the colloidal solid and it can be confirmed that the emulsion of droplets is stable and does not exhibit coalescence. Coalescence is apparent by the formation of large droplets visible to the eye, and ultimately by the formation of a layer of liquid monomers, polymer melt or polymer solution within the formulation. Physical stability of the composition during cure, polymerization, solvent evaporation or other polymer solidification is acceptable if no significant coalescence is evident and the solid polymer particles are present as a fine dispersion.

For example, in one embodiment the colloidal solids are employed in an amount of from 1 to 80%, particularly from 4 to 50% by weight of the dispersed phase. Mixtures of colloidal solids may be employed.

In one embodiment, one or more surfactants may optionally be used in addition to Pickering emulsion colloidal stabilizers, in order to conveniently control the size of the emulsion droplets in conjunction with the shear rate applied during the emulsification process. If present, the one or more surfactants are employed in an amount of from 0.1% to 90%, particularly from 1% to 60% by weight of the Pickering emulsion colloidal stabilizers. In a particular embodiment, the surfactants are chosen to have a low HLB such as 6 or below. In another particular embodiment, the surfactant is alkylamine 2-mole ethoxylate, whether the alkyl group contains from about 8 to about 18 carbon atoms.

The following examples illustrate further some of the aspects of the invention but are not intended to limit its scope. Where not otherwise specified throughout this specification and claims, percentages are by weight.

EXAMPLES 1-4

Illustrating the Use of Different Continuous Phase Liquids

A resin mixture A of 19.1 g 635 Thin Epoxy Resin (US Composites of West Palm Beach, Fla.) and 9.5 g 556 2:1 Epoxy Hardener (also of US Composites) was prepared. The following liquid continuous phase samples of 10 g liquid were then prepared each by vortex mixing with 0.2 g Aerosil 200 fumed silica as colloidal stabilizer: 9:1 ethylene glycol: water, 9:1 PEG200:water, 9:1 glycerine:water, and water. A 0.2 g of resin mixture A was then introduced into each continuous phase sample and dispersed by vortex mixing. The samples were placed on a platform shaker overnight at room temperature and then examined by light microscopy. In every case the presence of a dispersion of epoxy resin particles of diameter approximately 100 microns was confirmed. These examples show that small particles of solid epoxy resin may be formed in a variety of different liquid continuous aqueous phases.

EXAMPLES 5-7

Illustrating the Use of Different Colloids to Stabilize the Resin Before Curing

A resin mixture B was prepared by mixing together 9 g 635 Thin Epoxy Resin, 1.5 g of finely milled difenoconazole and 4.5 g 556 2:1 Epoxy Hardener. The following liquid continuous phases were then prepared each by vortex mixing: 0.2 g Aerosil 200 fumed silica in 9.8 g water, and 0.2 g fumed aluminum oxide in 9.8 g water. 0.2 g of resin mixture B was then introduced into each continuous phase sample and dispersed by vortex mixing. The samples were placed on a platform shaker overnight at room temperature and then examined by light microscopy. In every case the presence of a dispersion of fine epoxy resin particles of diameter approximately 100 microns was confirmed. In addition, a sample was prepared where the liquid continuous phase did not contain any colloidal solids, and the result was a large deposit of solid epoxy material adhered to the container wall. This example shows that a variety of different colloidal solids may be used to stabilize dispersions of epoxy resin but that if no colloidal solid is used the resin simply coalesces and ultimately solidifies into a solid mass.

EXAMPLES 8-16

Incorporating Different AI's into the Polymer Matrix

Nine different individual resin mixtures were prepared by mixing together 8 g 635 Thin Epoxy Resin, 4 g 556 2:1 Epoxy Hardener and between 1.0 and 1.5 g of the following finely milled active ingredients: atrazine, azoxystrobin, bicylopyrone, cyproconazole, difenoconazole, mesotrione, prodiamine, thiabendazole, thiamethoxam. By inspection it was clear that at these concentrations bicylopyrone and mesotrione were fully dissolved in the liquid resin, most of the cyproconazole was dissolved, and the other AI's had not appreciably dissolved. 1 g of each of these resin mixtures was separately dispersed by vortex mixing into 10 g continuous phase liquid samples each containing 0.2 g Aerosil 200 fumed silica dispersed in 9.8 g water. The samples were placed on a platform shaker overnight at room temperature and then examined by light microscopy. In every case the presence of a dispersion of epoxy resin particles of diameter approximately 100 microns was confirmed. Crystals of the active ingredient were visible inside the epoxy particles under polarized light, except that in the cases of bicyclopyrone and mesotrione individual crystals were not visible as these active ingredients had dissolved in the epoxy resin—in these cases the entire epoxy resin particle was slightly birefringent indicating the presence of crystal domains within the matrix. These examples show that a wide variety of different active ingredients may be efficiently captured in the epoxy resin particles, regardless of whether they are insoluble, partly-soluble or fully-soluble in the resin, and with no significant modification needed in the process nor the presence of other components.

EXAMPLES 17-18

Illustrating the Entrapment of an Active Ingredient in Polystyrene and Polyacrylate Matrices A. Formulation Preparation The dispersed phase is premixed with a shear mixer as described in table 1 below. The continuous phase is premixed with low shear mixer. The premixed dispersed phase is added into the continuous phase, and then blend with high shear mixer for 5-10 min. In order to polymerize, the emulsified formulation is treated with high temperature (70° C.) for 8 hr. Average diameter of particles was determined by Malvern® master sizer.

TABLE 1

|  | Example 17 | Example 18 |
| --- | --- | --- |
| Dispersed phase | Atrazine 6% Styrene monomer 14.7% Methyl ethyl ketone peroxide 0.3% | Atrazine 6% Methylmethacrylate monomer 14.7% Methyl ethyl ketone peroxide 0.3% |
| Continuous phase | Aerosil A300 3% Phosphoric acid (8%) 0.05% water 75.95% | Aerosil A300 3% Phosphoric acid (8%) 0.05% water 75.95% |
| Mean particle diameter (μm) | 13 | 14 |

EXAMPLES 19-20

Illustrating Control of Release Rate by Incorporation of a Mobile Non-Cross-Linkable Molecule into the Polymer Matrix and

EXAMPLES 21-22

Illustrating the Entrapment of Liquid Active Ingredients

A. Formulation preparation

The dispersed phase is premixed with a low shear mixer as described in table 2 below. The continuous phase is premixed with a low shear mixer. The premixed dispersed phase is added into the continuous phase, and then mix with a high shear mixer for 5-10 min. For accelerating the epoxy curing reaction, the mixed formulation was treated with high temperature (70° C.) for 3 hr. Average diameter of particles was determined by Malvern® master sizer.

B. Release Rate

The cured compositions 19 and 20 were diluted in water with appropriate emulsifiers (Toximul TA-6, Stepfac 8180 and Toximul 8320 etc) in a glass bottle and then stirred. The concentration of active ingredient was monitored by HPLC analysis.

EXAMPLES 21-24

Illustrating Pickering Emulsions Using Clay and Flocculating Polymers

A. Formulation Preparation

The dispersed phase is premixed with a shear mixer as described in table 3 below. The continuous phase is premixed with low shear mixer. The premixed dispersed phase is added into the continuous phase, and then blend with a high shear mixer for 5-10 min. In order to polymerize, the emulsified formulation is treated with high temperature (70° C.) for 8 hr. Average diameter of particles was determined by Malvern® master sizer.

TABLE 3

|  |  | 21 | 22 | 23 | 24 |
| --- | --- | --- | --- | --- | --- |
| Dispersed phase | Mefenoxam | 7.5 |  |  |  |
|  | s-metolachlor |  | 7.5 |  |  |
|  | Tefluthrin |  |  | 7.5 |  |
|  | Propiconazole |  |  |  | 7.5 |
|  | Resorcinol diglycidyl ether | 5 | 5 | 5 | 5 |
|  | Polyoxypropylene diamine (Mn = 230 Da) | 2.5 | 2.5 | 2.5 | 2.5 |
| Continuous phase | Clay (kaolin) | 1.2 | 1.2 | 1.2 | 1.2 |
|  | Xanthan Pregel (2%) | 2 | 2 | 2 | 2 |
|  | Phosphoric acid (8.5%) |  |  |  | 0.1 |
|  | water | 18.8 | 18.8 | 18.8 | 18.7 |
|  | Average Particle size (um) | 30 | 25 | 17 | 30 |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

TABLE 2

|  | Example 19 | Example 20 | Example 21 | Example 22 |
| --- | --- | --- | --- | --- |
| Dispersed phase | Thiamethoxam 5% Epoxy 635 10% Hardener 556 5% | Thiamethoxam 5% Epoxy 635 9% Hardener 556 4.5% Polyethyleneglycol (Mw = 200) 1.5% | Mefenoxam 5% Epoxy 635 10% Hardener 556 5% | s-metolachlor 5% Epoxy 635 10% Hardener 556 5% |
| Continuous phase | Aerosil A200 2% water 78% | Aerosil A200 2% water 78% | Aerosil A200 2% water 78% | Aerosil A200 2% water 78% |
| Average particle diameter (μm) | 55 | 45 | 25 | 27 |
| % ai release |  |  |  |  |
| 0 hr | 0.9 | 1.8 | 42 |  |
| 24 hrs | 1.2 | 2.3 | 51 |  |
| 48 hrs | 1.4 | 2.5 | 56 |  |

We claim:

1. An aqueous liquid dispersion concentrate composition comprising
   (a) a continuous aqueous liquid phase; and
   (b) at least one dispersed, solid phase comprising epoxy polymer matrix particles prepared from either a curable or polymerizable epoxy resin, and wherein:
      (i) the outside surfaces of the polymer matrix particles comprise a colloidal solid material; and
      (ii) the polymer matrix particles have at least one agrochemical active ingredient distributed within the polymer matrix particle.

2. The composition of claim 1, wherein the polymer matrix particles have a mean particle size of from 1 to 200 microns.

3. The composition of claim 1, wherein the colloidal solid material is present in an amount effective to stabilize the polymer matrix particles in an emulsion state during the process which is used to prepare the dispersed phase.

4. The composition of claim 1, wherein the agriculturally active ingredient comprises a solid.

5. The composition of claim 4, wherein the agrochemically active ingredient is atrazine.

6. The composition of claim 1, wherein the polymer molecules that comprise the polymer matrix particles contain hydrophilic groups that hydrate on exposure to water in a manner that renders the polymer matric particles more permeable such that they allow the active ingredient to diffuse out.

7. The composition of claim 1, wherein the continuous phase (a) comprises water and a substantially water-miscible, non-aqueous liquid.

8. The composition of claim 7, wherein the substantially water-miscible, non-aqueous liquid is selected from propylene carbonate, ethylene glycol, diethylene glycol, triethylene glycol, propylene glycol, dipropylene glycol, tripropylene glycol, butylene glycol, hexylene glycol, polyethylene glycols having a molecular weight of up to about 800, di(propylene glycol) methyl ether acetate, propylene glycol diacetate, triethyl phosphate, ethyl lactate, gamma-butyrolactone, propanol, tetrahydrofurfuryl alcohol, N-methyl pyrrolidone, dimethyl lactamide, and mixtures thereof.

9. The composition of claim 1, wherein the continuous phase (a) further comprises at least one agrochemically active ingredient and that active ingredient is in the state selected from a solution, an emulsion, a microemulsion, a suspension of microcapsules, or suspension of particles.

10. The composition of claim 1, wherein the continuous phase (a) further comprises one or more surfactants or dispersants.

11. The composition of claim 1, wherein the colloidal solid comprises a particulate inorganic material distributed at the surface of the polymer matrix particles.

12. The composition of claim 1, wherein the colloidal solid comprises an agrochemically active ingredient in fine particulate form and functional as a Pickering stabilizer that is distributed at the surface of the polymer matrix particles.

13. The composition of claim 1, wherein (b) comprises a cured epoxy resin polymer matrix prepared by curing an epoxy resin selected from di-and polyepoxide monomers, prepolymers, biodegradable epoxy resins or blends thereof with a hardener selected from primary and secondary amines and their adducts, cyanamide, dicyandiamide, polycarboxylic acids, anhydrides of polycarboxylic acids, polyamines, polyamino-amides, polyadducts of amines and polyepoxides, polyols and mixtures thereof.

14. The composition of claim 1, wherein the colloidal solid comprises no more than about 80 wt % of the dispersed solid phase.

15. The composition of claim 1, wherein the colloidal solid is a carbon black, a metal oxide, a metal hydroxide, a metal carbonates, a metal sulfates, a polymer, a silica or a clay.

16. The composition of claim 1, wherein the colloidal solid is a silica or a clay.

17. The composition of claim 1, wherein the agrochemically active ingredient is tefluthrin.

18. A method of preventing or combating infestation of plant species by pests, or regulating plant growth by diluting an effective amount of concentrate composition according to claim 1 with an aqueous liquid carrier selected from water and liquid fertilizer, and applying the dilute composition to the plant species or locus thereof.

* * * * *